US00PP14005P39

(12) United States Plant Patent
Amorao et al.

(10) Patent No.: US PP14,005 P3
(45) Date of Patent: Jul. 22, 2003

(54) STRAWBERRY PLANT NAMED 'DRISCOLL EL CAPITAN'

(75) Inventors: Amado Q. Amorao, Camarillo, CA (US); Arnoldo Solis, Jr., Oxnard, CA (US); Michael Ferguson, Chatsworth, CA (US)

(73) Assignee: Driscoll Strawberry Associtates, Inc., Watsonville, CA (US)

( * ) Notice: Subject to any disclaimer, the term of this patent is extended or adjusted under 35 U.S.C. 154(b) by 0 days.

(21) Appl. No.: 09/968,563

(22) Filed: Oct. 1, 2001

(65) Prior Publication Data

US 2003/0074703 P1 Apr. 17, 2003

(51) Int. Cl.[7] ..... A01H 5/00

(52) U.S. Cl. ..... Plt./209

(58) Field of Search ..... Plt./209

*Primary Examiner*—Bruce R. Campell
*Assistant Examiner*—Susan B. McCormick
(74) *Attorney, Agent, or Firm*—Pennie & Edmonds, LLP

(57) ABSTRACT

This invention relates to a new and distinct variety of strawberry named 'Driscoll El Capitan'. The variety is similar to the varieties Coronado and San Miguel. The variety is distinguished from 'Coronado' and 'San Miguel', in that 'Driscoll El Capitan' has an obtuse terminal leaflet teeth shape, medium to dense petiole pubescence, medium to strong anthocyanin coloration, cordate fruit shape, marked difference in shape between primary and secondary fruits, large hollow center size, and time of flowering is mid-December.

4 Drawing Sheets

1. BACKGROUND OF THE INVENTION

The new variety originated as a result of a controlled cross between the strawberry plants 'San Miguel' (U.S. Plant Pat. No. 10,642) and '12A71' (unpatented variety) in an ongoing breeding program, and was discovered as a seedling in Ventura County, Calif. in February, 1996. The original seedling of the new cultivar was asexually propagated by stolons in a nursery in Shasta County, Calif. Propagules were transplanted to a controlled breeding plot in Ventura County, Calif., where the variety was identified and selected for further evaluation. 'Driscoll El Capitan' was subsequently asexually propagated and underwent further testing at in Ventura County, Calif. for six years. This propagation and testing has demonstrated that the combination of traits disclosed herein which characterize the new variety are fixed and retained true to type through successive generations of asexual reproduction.

1.1 LATIN NAME OF THE GENUS AND SPECIES OF THE PLANT CLAIMED

The variety is botanically identified as *Fragaria*× *ananassa.*

2. SUMMARY OF THE INVENTION

The present invention relates to a new and distinct variety of strawberry named 'Driscoll El Capitan'. The variety is botanically identified as *Fragaria*×*ananassa.* The new variety is distinguished from other varieties by a number of characteristics as set forth in Tables 1–4.

3. COMPARISON TO SIMILAR VARIETIES

The varieties which we believe to be similar to 'Driscoll El Capitan' from those known to us are 'Coronado' (U.S. Plant Pat. No. 10,221) and 'San Miguel' (U.S. Plant Pat. No. 10,642). There are several characteristics of the new variety that are different from, or not possessed by 'Coronado' and 'San Miguel'. The new variety has an obtuse terminal leaflet teeth shape, medium to dense petiole pubescence, medium to strong anthocyanin coloration, cordate fruit shape, marked difference in shape between primary and secondary fruits, large hollow center size, and time of flowering is mid-December.

4. BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

5. DESCRIPTION OF THE NEW VARIETY

Figure 1:
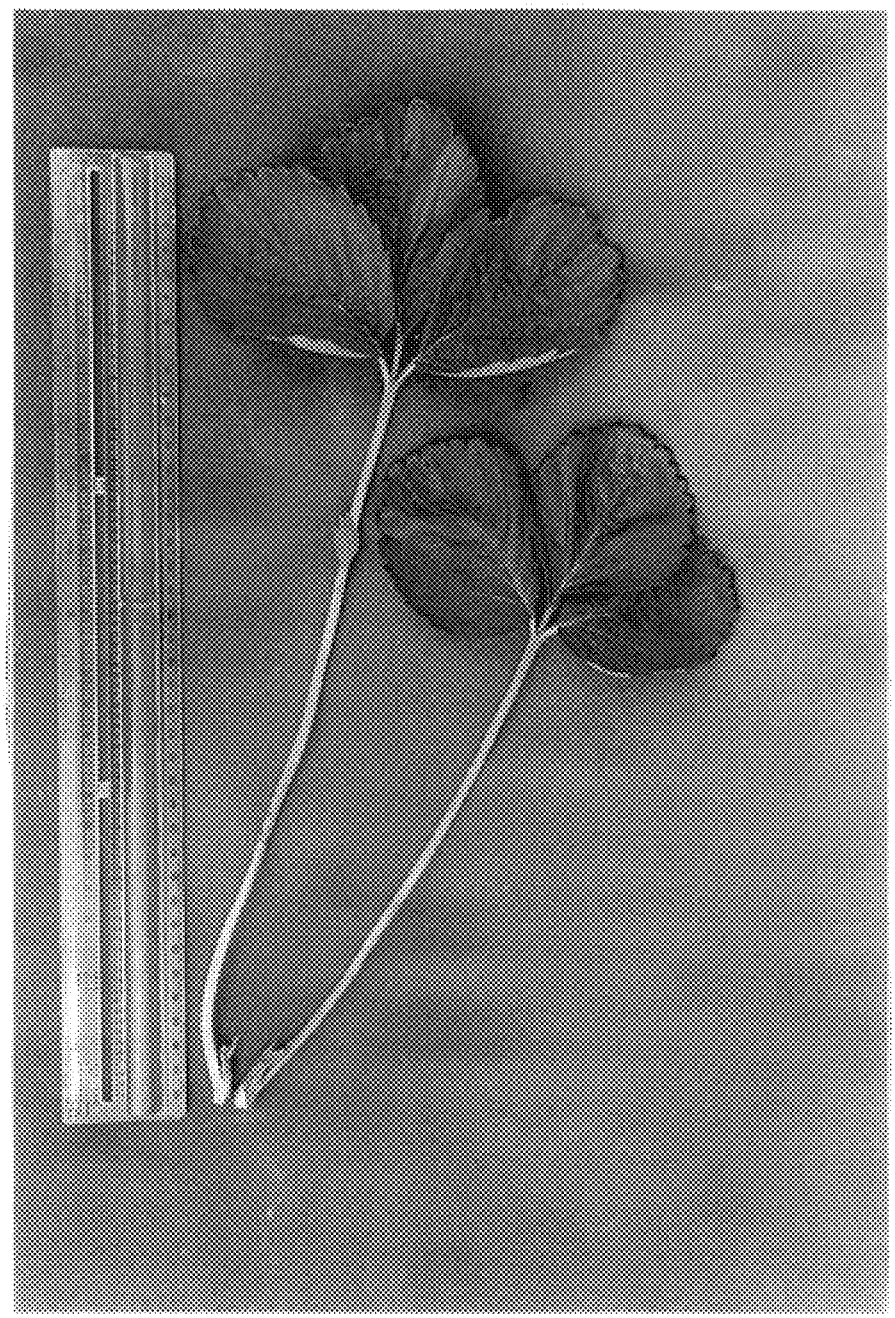
FIG. 1 shows the leaves of the plant.
Figure 2:
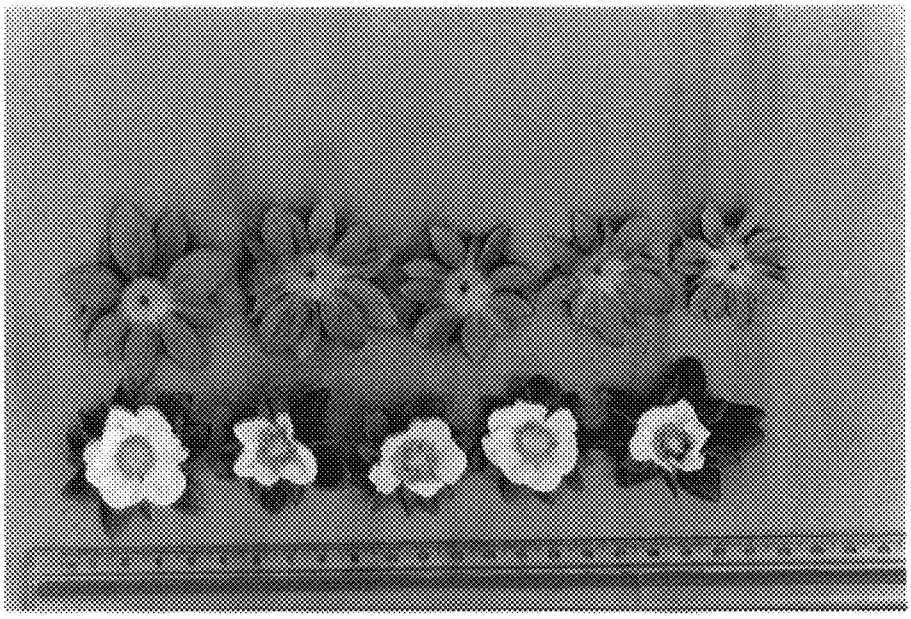
FIG. 2 shows the upper side and the under side of the flowers.
Figure 3:
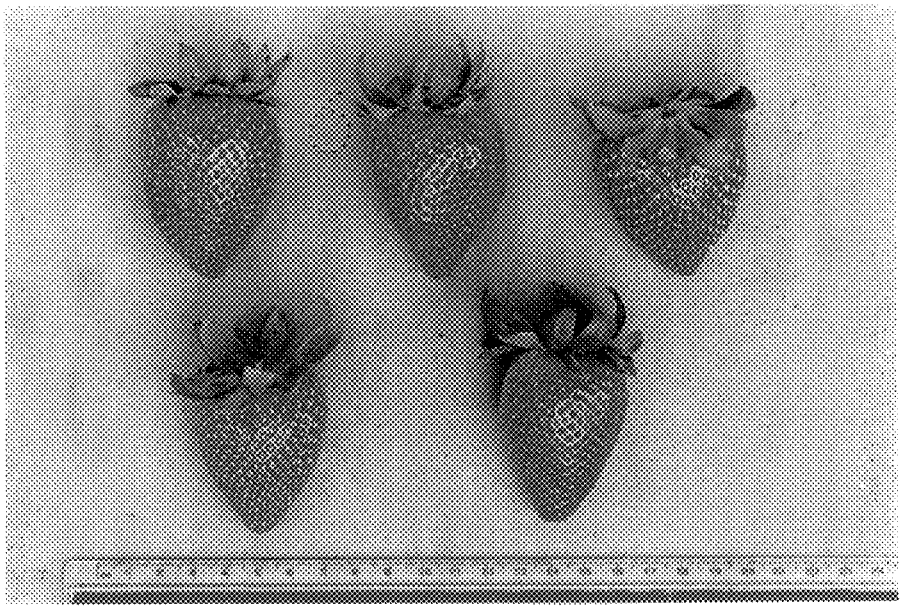
FIG. 3 shows a close-up of the fruit.
Figure 4:
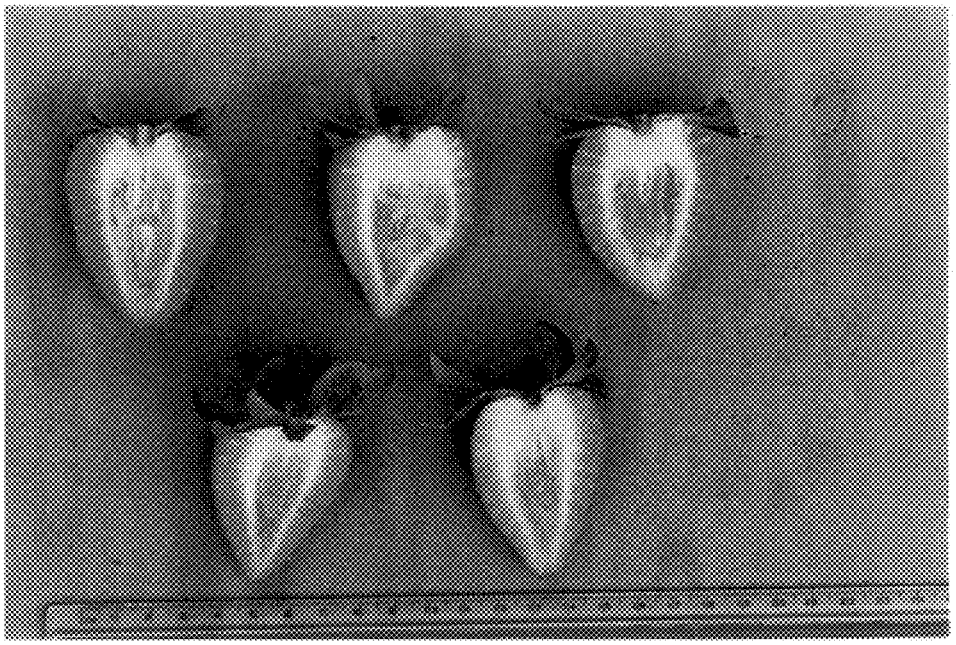
FIG. 4 shows the fruit in longitudinal cross-section.

The following detailed description of the new variety is based upon observations taken of plants and fruit grown in Monterey County, Calif., U.S.A. This description is in accordance with UPOV terminology. Observations of 'Driscoll El Capitan', 'Coronado' and 'San Miguel' were taken in side by side comparison in the year 2001. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

5.1 PROPAGATION

The new variety is principally propagated by way of stolons. Although propagation by stolons is presently preferred, other known methods of propagating strawberry plants may be employed.

5.2 CHARACTERISTICS OF THE NEW VARIETY

Information on the new variety is presented in Tables 1, 2, 3 and 4. In the tables, the flowers described are secondary flowers except where indicated. The petal color of 'Driscoll El Capitan' is white (155C in The R.H.S. Colour Chart). The fruit described is the secondary fruit on one-year-old plants. Fruit and flower measurements are an average of both primary and secondary fruit and flowers. The average stolon diameter at bract subtending the daughter plant is 2.40 mm. The number of propagules/nursery plant in 2002 was 61.8. The anthocyanin coloration of the stipules in the Fall of the year in nursery is light green with a faint blush of pink anthocyanin (149D in The R.H.S. Colour Chart). The petiolule length is 9.47 mm and the petiolule color is 149A. The leaf texture is blistered, the leaf margin is crenate, the leaf vein color is 149A (in The R.H.S. Colour Chart), and the leaf venation is pinnate. The petal shape is ovate to rounded, the petal margin is entire, the petal number is 6, and the petal color of upper and lower surface is 155C (in The R.H.S. Colour Chart). The sepal color is 137B (in The R.H.S. Colour Chart) on the upper surface and 137D (in The R.H.S. Colour Chart) on the lower surface, the average sepal number is 11.7, average sepal length is 13.98 mm, and average sepal width as 6.90 mm. The color of fruit vascular tissue is 155C (in The R.H.S. Colour Chart). The average weight of achenes is 0.00064 g and the average number of achenes/berry is 252.5. The anthocyanin color of stolon is purple red 58A (in The R.H.S. Colour Chart). The color of anthers is yellow 13A (in the R.H.S. Colour Chart) and the color of pistils and receptical is yellow 7A (in The R.H.S. Colour Chart).

Table 1 provides information on the plant and fruit characteristics of the new variety 'Driscoll El Capitan' compared with characteristics of 'Coronado' and 'San Miguel'. Table 2 provides additional information of the plant and fruit characteristics of the new variety 'Driscoll El Capitan' compared with characteristics of the varieties 'Coronado' and 'San Miguel'. Table 3 provides reactions of the new variety to stresses, pests and diseases compared with reactions of the varieties 'Coronado' and 'San Miguel'. Table 4 provides isozyme characteristics of the new variety as compared to that of the varieties 'Coronado' and 'San Miguel'.

TABLE 1

DETAILED COMPARISON OF 'DRISCOLL EL CAPITAN', 'CORONADO' AND 'SAN MIGUEL'

| | 'Drsicoll El Capitan' | 'Coronado' | 'San Miguel' |
|---|---|---|---|
| Plant Characteristics | | | |
| Height of Plant (cm) | 24.0 | 20.7 | 22.8 |
| Spread of Plant (cm) | 32.6 | 28.7 | 29.4 |
| Number of Crowns | 6.0 | 4.6 | 4.4 |

TABLE 1-continued

DETAILED COMPARISON OF 'DRISCOLL EL CAPITAN', 'CORONADO' AND 'SAN MIGUEL'

| | 'Drsicoll El Capitan' | 'Coronado' | 'San Miguel' |
|---|---|---|---|
| Leaf Characteristics | | | |
| Terminal Leaflet Length (cm) | 6.0 | 6.1 | 6.2 |
| Terminal Leaflet Width (cm) | 6.0 | 6.3 | 5.8 |
| Terminal Leaflet Length/Width | 1.00 | 0.97 | 1.07 |
| # Teeth/Terminal Leaflet | 16.3 | 21.6 | 20.7 |
| Color of upper side | dark green 147A | light to medium green 137A | medium to dark green 147A |
| Color of under side | light to medium green 147C | light to medium green 137B | light to medium green 138B |
| Petiole Length (cm) | 18.2 | 16.3 | 16.0 |
| Petiole Color | 149A | 149A | 149A |
| Bract Frequency | 8% typically single | 0% | 30% typically paired |
| Stipule Length (cm) | 3.4 | 3.4 | 2.9 |
| Stipule Width (cm) | 1.1 | 1.2 | 1.1 |
| Flower Characteristics | | | |
| Petal Length (cm) | 1.5 | 1.6 | 1.4 |
| Petal Width (cm) | 1.7 | 1.7 | 1.5 |
| Petal Length/Width Ratio | 0.91 | 0.93 | 0.98 |
| Flower Diameter (cm) | 3.2 | 3.4 | 2.7 |
| Calyx Diameter (cm) | 4.4 | 4.4 | 4.1 |
| Fruiting Truss | | | |
| Length (cm) | 22.9 | 22.1 | 25.7 |
| Fruit Characteristics | | | |
| Fruit Length (cm) | 5.0 | 4.3 | 4.3 |
| Fruit Width (cm) | 3.9 | 3.9 | 4.1 |
| Fruit Length/Width Ratio | 1.28 | 1.11 | 1.07 |
| Average Berry Weight (g) | 23.3 | 23.6 | 23.2 |
| External Color | dark red 53A | red 46A | dark red 53A |
| Internal Color | red 43A | red 41A | dark red 45A |
| Average % brix | 7.9 | 7.1 | 7.1 |
| Brix/Acid Ratio | 9.71 | 9.11 | 9.33 |
| Achene Coloration | dark red to yellow green 60A to 151A | dark red to yellow 53A to 141B | dark red to yellow green 53A to 151B |
| Yield (g/plant) | 695 | 598 | 557 |

TABLE 2

CHARACTERISTICS OF 'DRISCOLL EL CAPITAN', 'CORONADO' AND 'SAN MIGUEL'

| | 'Driscoll El Capitan' | 'Coronado' | 'San Miguel' |
|---|---|---|---|
| Plant | | | |
| Habit | globase | globase | flat globase |
| Density | open | open | open |
| Vigor | strong | medium | medium |

TABLE 2-continued

CHARACTERISTICS OF 'DRISCOLL EL CAPITAN', 'CORONADO' AND 'SAN MIGUEL'

| | 'Driscoll El Capitan' | 'Coronado' | 'San Miguel' |
|---|---|---|---|
| Leaf | | | |
| Shape in cross section | concave | slightly concave | concave |
| Interveinal blistering | medium | strong | strong |
| Glossiness | medium strong | strong | strong |
| Number of leaflets | three only | more than three on up to 5 out of 10 leaves | three only |
| Terminal leaflet margin profile | flat | flat to cupped | flat to revolute |
| Terminal leaflet shape of base | obtuse | obtuse | rounded |
| Terminal leaflet shape of teeth | obtuse | rounded | rounded |
| Stipule pubescence | sparse | sparse | sparse |
| Petiole pubescence | medium to dense | medium | sparse to medium |
| Petiole pose of hairs | outward | outward | outward |
| Stolon | | | |
| Amount | many | medium to many | many |
| Anthocyanin coloration | medium to strong | weak to medium | weak to medium |
| Thickness | thin | medium | thin to medium |
| Pubescence | sparse to medium | sparse to medium | sparse to medium |
| Inflorescence | | | |
| Position relative to foilage | above | level to above | above |
| Diameter of calyx relative to corolla on secondary flowers | larger | larger | larger |
| Diameter of inner calyx relative to outer secondary flowers | smaller to same size | same size to larger | same size |
| Spacing of petals | overlapping | touching to overlapping | overlapping |
| Fruiting Truss | | | |
| Attitude at first picking | prostrate | semi-erect to prostrate | prostrate |
| Fruit | | | |
| Predominant shape | cordate | conical to wedged | conical to cylindrical |
| Difference in shapes between primary and secondary fruits | marked | moderate | moderate |
| Band without achenes | very narrow | narrow | very narrow |
| Unevenness of surface | weak to medium | weak to medium | weak to medium |
| Evenness of color | slightly uneven to even | even | even |
| Glossiness | strong | medium to strong | medium |
| Insertion of achenes | below to level with the surface | below surface | below surface |
| Insertion of calyx | in a basin to level | level to set above | set above |
| Pose of the calyx segments | reflexed | spreading | spreading to reflexed |
| Size of calyx in relation to fruit on secondary fruit | larger | larger | same size |
| Adherence of calyx | strong | medium | strong |
| Firmness of flesh | firm | firm | firm |

TABLE 2-continued

CHARACTERISTICS OF 'DRISCOLL EL CAPITAN', 'CORONADO' AND 'SAN MIGUEL'

| | 'Driscoll El Capitan' | 'Coronado' | 'San Miguel' |
|---|---|---|---|
| Evenness of flesh color | even | slightly even | even |
| Distribution of flesh color | marginal and central | marginal and central | marginal and central |
| Hollow center size | large | medium | medium |
| Sweetness | strong | weak | strong |
| Texture when tested | fine | fine | fine |
| Acidity | medium | strong | medium |
| Time of Flowering | mid-December | early-January | early-January |
| Harvest Interval in 2001 | late-January to mid-June | early-February to mid-June | early-February to mid-June |
| Type of Bearing | partially everbearing | partially everbearing | partially everbearing |

5.3 REACTION TO STRESS, PESTS AND DISEASE

TABLE 3

| | 'Driscoll El Capitan' | 'Coronado' | 'San Miguel' |
|---|---|---|---|
| Reaction to Stress | | | |
| high pH | moderately resistant | moderately resistant | moderately resistant |
| high soil salt levels | moderately resistant | moderately resistant | moderately resistant |
| Reaction to Pests | | | |
| *Tetranychus urticae* | moderately resistant | moderately resistant | moderately resistant |
| *Lygus hesperus* | susceptible | susceptible | susceptible |
| Reaction To Diseases | | | |
| Botrytis fruit rot | moderately susceptible | moderately susceptible | moderately susceptible |
| Powdery mildew | moderately resistant | moderately resistant | moderately resistant |
| Verticillium wilt | susceptible | susceptible | susceptible |
| Strawberry Mottle Virus | moderately resistant | moderately resistant | moderately resistant |
| *Xanthomonas fragariae* | moderately susceptible | moderately susceptible | moderately susceptible |

5.4 ISOZYME ANALYSIS

In addition to the morphological description above, the new cultivar 'Driscoll El Capitan' has been analyzed to obtain an indication of its genetic makeup to provide further means for identifying the new variety and distinguishing it from other somewhat similar and/or related strawberry varieties. Specifically, leaf samples of 'Driscoll El Capitan', 'Coronado' and 'San Miguel' were analyzed by electrophoresis for isozyme patterns of the enzymes phosphoglucoisomerase ("PGI"), leucine aminopeptidase ("LAP") and phosphoglucomutase ("PGM"). See *J. Amer. Soc. Hort. Sci.* 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL EL CAPITAN', 'CORONADO' AND 'SAN MIGUEL'

| Locus | 'Driscoll El Capitan' | 'Coronado' | 'San Miguel' |
|---|---|---|---|
| PGI | A2 | A2 | A4 |
| LAP | B3 | B3 | B3 |
| PGM | C4 | C4 | C2 |

What is claimed is:

1. A new and distinct variety of strawberry plant, substantially as shown and described.

* * * * *